United States Patent [19]

Ripke

[11] Patent Number: 5,212,292
[45] Date of Patent: May 18, 1993

[54] PROCESS FOR THE PREPARATION OF LIGHT-COLORED ALKYL POLYGLYCOSIDES

[75] Inventor: Norbert Ripke, Haltern, Fed. Rep. of Germany

[73] Assignee: Huels Aktiengesellschaft-PB 15, Marl, Fed. Rep. of Germany

[21] Appl. No.: 792,597

[22] Filed: Nov. 15, 1991

[30] Foreign Application Priority Data

Feb. 15, 1991 [DE] Fed. Rep. of Germany ....... 4104640

[51] Int. Cl.$^5$ .................. C07H 1/00; C07H 15/04; C07G 3/00
[52] U.S. Cl. .................. 536/18.6; 536/18.5; 536/4.1; 536/124
[58] Field of Search ........ 536/18.6, 18.5, 124, 536/4.1

[56] References Cited

U.S. PATENT DOCUMENTS

| | | |
|---|---|---|
| H619 | 4/1989 | McDaniel, Jr. et al. ......... 536/18.6 |
| 3,974,138 | 8/1976 | Lew .................................. 536/18.6 |
| 4,483,979 | 11/1984 | Mao ................................. 536/18.6 |
| 4,557,729 | 12/1985 | McDaniel, Jr. et al. ......... 536/18.5 |
| 4,820,814 | 4/1989 | Lueders ............................ 536/18.6 |
| 4,939,245 | 7/1990 | Rasche et al. ..................... 536/18.5 |
| 4,950,743 | 8/1990 | McCurry, Jr. et al. .......... 536/18.5 |
| 4,990,605 | 2/1991 | Lueders ............................ 536/18.6 |

*Primary Examiner*—Michael G. Wityshyn
*Assistant Examiner*—Louise N. Leary
*Attorney, Agent, or Firm*—Oblon, Spivak, McClelland, Maier & Neustadt

[57] ABSTRACT

A process for the preparation of alkyl polyglycosides containing an alkyl group of about 8 to 24 carbon atoms, which comprises glycosylating and transglycosylating one or more saccharides, wherein the glycosylation is carried out in an evaporator at an acid number of about 1 to 10 mg of KOH/g.

15 Claims, No Drawings

PROCESS FOR THE PREPARATION OF LIGHT-COLORED ALKYL POLYGLYCOSIDES

BACKGROUND OF THE INVENTION

1. Field of the Invention

The present invention relates to a process for the preparation of alkyl polyglycosides containing an alkyl group of 8 to 24 carbon atoms, in which saccharides are glycosylated and the products obtained are transglycosylated.

2. Description of the Invention

Alkyl polyglycosides are non-poisonous and easily degradable surface-active substances. They are, therefore, used as detergents and cleaning agents and as emulsifiers and dispersants. However, they only exhibit the desired surface properties if the alkyl groups have at least 8 carbon atoms.

Alkyl polyglycosides containing long-chain alkyl radicals can be prepared entirely or in part from renewable raw materials. Due to their interesting surfactant properties in combination with very good biodegradability, these alkyl polyglycosides are gaining increased importance. These products must, necessarily, meet high aesthetic requirements for household and cosmetic application. Thus, processes by which alkyl polyglycosides can be prepared in transparent aqueous solutions of attractive color are of great interest.

Alkyl polyglycosides are, in general, prepared from saccharides and alcohols by glycosylation and transglycosylation. In a two-step process, for example, an n-butyl glycoside is first prepared by glycosylation with n-butanol, which is then converted into the desired long-chain alkyl polyglycoside by transglycosylation with a long-chain alcohol. However, the products obtained in this process are dark-colored unless additional measures are taken.

The color can be improved according to U.S. Pat. No. 4,762,918 by catalytic hydrogenation.

When long-chain alkyl saccharides are prepared, the hydroxy polycarboxylic acids citric acid, tartaric acid and malic acid can, according to U.S. Pat. No. 4,465,828, also contribute to the improvement in color.

According to EP 0,077,167, in the reaction of alcohols with aldoses or ketoses reducing agents, such as hypophosphorous acid or sulphurous acid, can also be added. These additives are advantageous at virtually every point in the process. They improve the color of the alkyl glycosides.

Preventive measures are also known. Thus, according to EP 0,102,558, $C_3$- to $C_5$-alkyl glucosides of improved color are obtained by carrying out the glucosylation in the presence of an alkali metal salt of boric acid.

According to EP 0,165,721, the color of the products can be improved by multi-step bleaching using hydrogen peroxide and stabilized by the addition of compounds releasing sulfur dioxide.

Due to the high costs of catalysts and the difficult reaction procedure, catalytic hydrogenation is problematical. In large-scale processes, hydrogen peroxide bleaching requires the storage and handling of large amounts of peroxide. In the case of all solid and liquid color-improving agents, it is furthermore difficult to remove these agents quantitatively after reaction is complete.

In EP 0,092,876, the product, after transglycosylation and neutralization are complete, is purified by distilling off the excess long-chain alcohols having 12 to 18 carbon atoms in a thin-film evaporator. However, in this subsequent purification process, dye formation during glycosylation or transglycosylation is not prevented.

Thus, a need exists for a process for preparing alkyl polyglycosides which are light-colored in which dye formation is suppressed even during glycosylation without using auxiliary substances.

SUMMARY OF THE INVENTION

Accordingly, it is an object of the present invention to provide a process for preparing alkyl polyglycosides in which dye formation is suppressed.

It is also an object of the present invention to provide such a process which avoids the use of auxiliary substances to suppress dye formation.

The above objects and others which will become more apparent in view of the following disclosure are provided by a process for preparing alkyl polyglycosides containing an alkyl group of about 8 to 24 carbon atoms which entails glycosylating and transglycosylating one or more saccharides, wherein the glycosylation is carried out in an evaporator at an acid number of about 1 to 10 mg of KOH/g.

DETAILED DESCRIPTION OF THE PREFERRED EMBODIMENTS

In accordance with the present invention, it has been surprisingly discovered that the rapid removal of water formed during glycosylation and introduced for glycosylation contributes to the improvement of the color of the alkyl polyglycosides.

More particularly, it has been surprisingly discovered that by carrying out the glycosylation in an evaporator at an acid number (AN) of about 1 to 10 mg of KOH/g, dye formation can be suppressed even during glycosylation without using foreign auxiliary substances which would subsequently have to be recovered.

Examples of suitable evaporators for the process according to the invention are tubular, tube bundle, falling-film and thin-film evaporators. Of these, falling-film and thin-film evaporators are preferably used. Glycosylation mixtures can be subjected in these evaporators to flash evaporation which is gentle on the products.

For glycosylation, in general, a saccharide, short-chain alcohol of about 1 to 5 carbon atoms and acid catalyst are mixed and then heated, thereby initiating the reaction with the formation of water.

The saccharides used can be monosaccharides, such as glucose, mannose, gulose, galactose or talose, but also di-and oligosaccharides having up to about 10 saccharide units may be used. The units can have a 1,2-, 1,3-, 1,4- or 1,60-linkage. $\alpha$- or $\beta$-linkages may also be present. The chains can be linear or branched. Preferably, glucose is used. Water-containing products may also be introduced into the reaction.

Examples of short-chain alcohols which can be used are ethanol, propanol, butanol, pentanol, but also glycols, such as ethylene glycol and propylene glycol, for example.

The acid catalysts used may be mineral acids, such as sulfuric or phosphoric acid, for example. Organic acids, such as, for example, aryl-, alkyl- or aralkylsulphonic acids may also be used.

During glycosylation, the AN is preferably in the range from about 1.5 to 5 mg of KOH/G.

The reaction is preferably carried out at a product temperature of about 60° to 160° C. A temperature range from about 80° to 120° C. is particularly preferred. In a particular embodiment, care is taken that the product temperature at the evaporator outlet is about 80° to 120° C. The reaction can be carried out at atmospheric pressure, at a slightly reduced pressure and also at superatmospheric pressure.

The evaporators are preferably operated at a heating temperature of about 120° to 180° C.

The alkyl glycosides containing short-chain alkyl groups obtained during glycosylation are subsequently converted to alkyl polyglycosides by transglycosylation with long-chain alcohols having 8 to 24 C atoms. Transglycosylation can be carried out by known methods.

The alcohols used here can be linear. However, they can also contain branchings. They can be saturated or also contain olefinic double bonds. Natural or synthetic fatty alcohols or fatty alcohol mixtures can be used. Examples are decanol, 10-undecen-1-ol, dodecanol, myristyl alcohol and stearyl alcohol. The alcohols preferably contain about 10 to 18 carbon atoms.

The alkyl polyglycosides prepared have an average degree of polymerization of about 1 to 10. Of these, low average degrees of polymerization of about 1.3 to 5 are preferred.

The process according to the invention has the following surprising advantages:

1. The water is rapidly separated off. This accelerates glycosylation. The space-time yield is increased.

2. The product is subjected to less thermal stress. Damage of the product due to acid hydrolysis is significantly reduced. For this reason, alkyl polyglycosides of improved color are obtained.

Although the reaction mixture from glycosylation is not neutralized, no baked-on deposits or blockages occur in the evaporator.

In general, the process is carried out in such a manner that the mixture freshly prepared for glycosylation is directly introduced into a heat exchanger functioning as an evaporator. The reaction mixture is then circulated through the heat exchanger about 5 to 20 times. This remove the water within a very short period of time in an efficient manner.

The present invention will now be further illustrated by reference to certain examples which are provided for purposes of illustration and are not intended to be limitative.

EXAMPLE 1

1 kg of butyl glucoside in 4 l of butanol is initially introduced at 118° C. into a 5 l stirred reactor fitted with column and water separator. The mixture is stirred and, at the same time, pumped through a falling-film evaporator (area of 0.2 m², oil temperature of 160° C.) at a volume stream of 22 l/h and returned to the stirred reactor. Before entry into the evaporator, 1 l of glucose syrup (60% strength in water), 12.5 g of $H_2SO_4$ and 3 l of butanol are added to the circulated product via a static mixer.

Product temperature at the evaporator outlet: 116° C.
AN in the stirred reactor: 2 mg of KOH/G.

Butanol and water ar distilled off and separated in the water separator. Butanol is returned.

In the run-off from the evaporator, the water content in the product is already less than 1%.

After a reaction time of 1.25 hours at 118° C. (product temperature in the reactor) and atmospheric pressure, the reaction is complete.

Iodine color number (ICN) of butyl glucoside: 60 to 80 (from a 35% strength solution, in butanol)

For subsequent transglycosylation, 2 kg of butyl glucoside (ICN: 60 to 80) and a further 12.5 g of $H_2SO_4$ are reacted at 116° C. and 400 hPA with 3 l of a mixture of 70% of dodecanol and 30% of tetradecanol. Butanol is removed by distillation. After about 2 hours, the reaction is complete. The mixture is then neutralized, after which excess alcohol is removed by distillation. The solid obtained is dissolved in water and bleached with ozone, giving a light-colored alkyl polyglucoside.
Average degree of polymerization: 1.65
ICN: 3 to 5 (from a 50% strength aqueous solution)

Comparative Example A

The procedure is as in Example 1. However, glucosylation is carried out in a 10 l stirred reactor equipped with a water separator at 118° C. over a period of 4 hours, the stirred mixture being subjected to distillation.
ICN of butyl glucoside: 100 to 200 (from a 35% strength solution in butanol)

The alkyl polyglucoside prepared according to Example 1 using this butyl glucoside has the following properties:
Average degree of polymerization: 1.65
ICN: 20 (from a 50% strength aqueous solution)

Having described the present invention, it will be apparent to one of ordinary skill in the art that many changes and modifications may be made to the above-described embodiments without department from the spirit and the scope of the present invention.

What is claimed as new and desired to be served by Letters Patent of the United States is:

1. In a process for the preparation of alkyl polyglycosides containing an alkyl group of about 8 to 24 carbon atoms, which comprises glycosylating one or more saccharides by mixing said one or more saccharides, an alcohol or glycol of about 1 to 5 carbon atoms and an acid catalyst and then heating the same and transglycosylating the product resulting therefrom with long-chain alcohols having 8 to 24 carbon atoms, the improvement wherein the glycosylating is carried out in an evaporator at an acid number of about 1 to 10 mg of KOH/g.

2. The process according to claim 1, wherein the glycosylation is carried out in a falling-film or thin-film evaporator.

3. The process according to claim 1, wherein the acid number is set to about 1.5 to 5 mg of KOH/g.

4. The process according to claim 1, wherein the glycosylation is carried out in an evaporator heated to about 120° to 180° C.

5. The process according to claim 1, wherein the product temperature during glycosylation is about 60° to 160° C.

6. The process according to claim 5, wherein the product temperature is about 80° to 120° C.

7. The process according to claim 1, wherein the alkyl polyglycosides formed have an average degree of polymerization of about 1 to 10.

8. The process according to claim 7, wherein the alkyl polyglycosides formed have an average degree of polymerization of about 1.3 to 5.

9. The process according to claim 1, which further comprises conducting the glycosylation in a heat exchanger functioning as an evaporator.

10. The process according to claim 1, wherein said one or more saccharides comprise monosaccharides or oligosaccharides.

11. The process according to claim 10, wherein said monosaccharides are selected from the group consisting of glucose, mannose, gulose, galactose and talose.

12. The process according to claim 10, wherein said oligosaccharides have up to about 10 carbon atoms.

13. The process according to claim 1, wherein said alcohol is ethanol, propanol, butanol or pentanol.

14. The process according to claim 1, wherein said glycol is ethylene glycol or propylene glycol.

15. The process according to claim 1, wherein said acid catalyst is a mineral acid or an organic acid effective for catalyzing the glycosylation.

* * * * *